United States Patent
Nogueiras Nieto et al.

(10) Patent No.: US 12,409,165 B2
(45) Date of Patent: Sep. 9, 2025

(54) PHARMACEUTICAL COMPOSITION COMPRISING ELTROMBOPAG BIS(MONOETHANOLAMINE)

(71) Applicant: SYNTHON B.V., Nijmegen (NL)

(72) Inventors: Luis Nogueiras Nieto, Sant Boi de Llobregat (ES); Lisardo Alvarez Fernandez, Sant Boi de Llobregat (ES); Rohit Kumar, Sant Boi de Llobregat (ES)

(73) Assignee: Synthon B.V., Nijmegen (NL)

( * ) Notice: Subject to any disclaimer, the term of this patent is extended or adjusted under 35 U.S.C. 154(b) by 565 days.

(21) Appl. No.: 17/782,425

(22) PCT Filed: Dec. 4, 2020

(86) PCT No.: PCT/EP2020/084723
§ 371 (c)(1),
(2) Date: Jun. 3, 2022

(87) PCT Pub. No.: WO2021/110959
PCT Pub. Date: Jun. 10, 2021

(65) Prior Publication Data
US 2023/0022228 A1    Jan. 26, 2023

(30) Foreign Application Priority Data

Dec. 6, 2019  (EP) .................... 19214295

(51) Int. Cl.
| | | |
|---|---|---|
| *A61K 31/4152* | (2006.01) | |
| *A61K 9/00* | (2006.01) | |
| *A61K 9/20* | (2006.01) | |
| *A61K 9/28* | (2006.01) | |

(52) U.S. Cl.
CPC ........ *A61K 31/4152* (2013.01); *A61K 9/0053* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2833* (2013.01)

(58) Field of Classification Search
CPC . A61K 31/4152; A61K 9/2018; A61K 9/2077
See application file for complete search history.

(56) References Cited

FOREIGN PATENT DOCUMENTS

| | | | | |
|---|---|---|---|---|
| CN | 107693515 | | 2/2018 | |
| WO | WO 01/89457 | | 11/2001 | |
| WO | WO 2008/136843 | | 11/2008 | |
| WO | WO-2008136843 | A1 * | 11/2008 | ......... A61K 31/4152 |
| WO | WO 2015/029074 | | 3/2015 | |
| WO | WO 2018/078644 | | 3/2018 | |
| WO | WO-2018078644 | A1 * | 5/2018 | ......... A61K 31/4152 |
| WO | WO 2018/197088 | | 11/2018 | |
| WO | WO-2018197088 | A1 * | 11/2018 | ......... A61K 31/4152 |
| WO | WO 2019/086725 | | 5/2019 | |

OTHER PUBLICATIONS

Shanmugam, S. "Granulation techniques and technologies: recent progresses" BioImpacts, 2015, 5(1), 55-63 (Year: 2015).*
Luhn et al. https://www.pharmaexcipients.com/wp-content/uploads/attachments/Pharma_poster_Sensorik_A0_portrait.pdf?t=1442598355; available online Sep. 18, 2015 (Year: 2015).*

* cited by examiner

*Primary Examiner* — Andrew S Rosenthal
(74) *Attorney, Agent, or Firm* — Buscher Patent PLLC

(57) ABSTRACT

The present invention relates to a film-coated swallowable tablet comprising eltrombopag bis(monoethanolamine) and pharmaceutically acceptable excipients comprising calcium silicate as diluent. The invention further relates to the use of said tablet as a medicament, particularly in the treatment of immune thrombocytopenia (ITP), thrombocytopenia in patients with chronic hepatitis C virus (HCV) and severe aplastic anaemia (SAA).

17 Claims, No Drawings

PHARMACEUTICAL COMPOSITION COMPRISING ELTROMBOPAG BIS(MONOETHANOLAMINE)

BACKGROUND OF THE PRESENT INVENTION

Eltrombopag bis(monoethanolamine), chemically 3'-{(2Z)-2-[1-(3,4-dimethylphenyl)-3-methyl-5-oxo-1,5-dihydro-4H-pyrazol-4-ylidene]hydrazino}-2'-hydroxy-3-biphenyl-carboxylic acid bis(monoethanolamine) of formula (I),

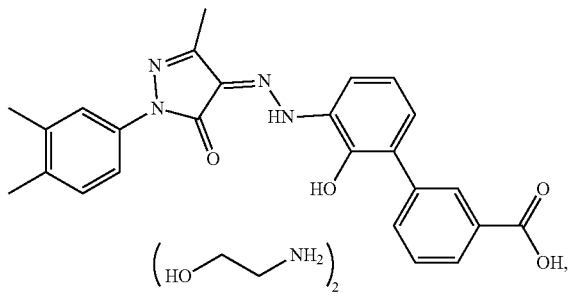

is a pharmaceutically active compound. It is used for the treatment of immune thrombocytopenia (ITP), thrombocytopenia in patients with chronic hepatitis C virus (HCV) and severe aplastic anaemia (SAA).

Eltrombopag bis(monoethanolamine), also known as eltrombopag olamine, is marketed by Novartis under the brand names Revolade® in Europe and Promacta® in the US and is disclosed in WO2001089457. Revolade® and Promacta® are supplied as immediate release film-coated tablets. Revolade® is available in three strengths: 25, 50 and 75 mg. Promacta® is available in five strengths: 12.5, 25, 50, 75 and 100 mg. The tablet composition of the different strengths is not dose proportional.

Eltrombopag bis(monoethanolamine) exhibits low solubility and medium permeability. WO2008136843 discloses the pharmaceutical composition of the Revolade®/Promacta® tablets. The Revolade®/Promacta® tablet formulation comprises, besides eltrombopag bis(monoethanolamine), the diluents microcrystalline cellulose and mannitol. According to WO2008136843, the use of diluents comprising reducing sugars or coordinating metals should be avoided because of the fact that these compounds may undergo a Maillard reaction or form an insoluble metal complex with eltrombopag bis(monoethanolamine).

WO2015029074 discloses compositions comprising eltrombopag olamine and more than 12% by weight based on the total weight of the composition of a disintegrant.

CN107693515 discloses pharmaceutical compositions comprising eltrombopag, or a salt thereof, and at least one alkalizing agent comprising a monovalent acid salt of a weak acid or a monovalent metal hydroxide. The dissolution rate is improved by using the alkalizing agent.

WO2018197088 discloses pharmaceutical tablet compositions comprising eltrombopag olamine and one or more reducing sugars selected from the group consisting of lactose, maltose, glucose, arabinose and fructose, wherein eltrombopag olamine is present in the intragranular phase and the reducing sugar in the extragranular phase or vice versa.

WO2019086725 discloses compositions comprising eltrombopag olamine, one or more reducing sugars selected from the group consisting of lactose, maltose, glucose, arabinose and fructose, and one or more semisynthetic and/or synthetic polymer binder agent. The composition is obtained by granulation. Eltrombopag olamine, the reducing sugar(s) and binder agent(s) are all present in the intragranular or extragranular composition.

It would be desirable to have a tablet composition comprising eltrombopag bis(monoethanolamine) that exhibits adequate dissolution and disintegration. The composition should exhibit excellent stability, be suitable for production on commercial scale and bioequivalent to Revolade®/Promacta®. Furthermore, it would be advantageous if the different tablet strengths can be formulated in a dose proportional manner to require just one single blend.

BRIEF DESCRIPTION OF THE PRESENT INVENTION

The present invention provides a film-coated swallowable tablet comprising eltrombopag bis(monoethanolamine) and pharmaceutically acceptable excipients comprising calcium silicate as diluent.

It also provides a process to prepare the tablet comprising wet granulation.

Said pharmaceutical composition may be used as a medicament, particularly in the treatment of immune thrombocytopenia (ITP), thrombocytopenia in patients with chronic hepatitis C virus (HCV) and severe aplastic anaemia (SAA).

DETAILED DESCRIPTION OF THE PRESENT INVENTION

The film-coated tablet Revolade®/Promacta® comprises, besides eltrombopag bis(monoethanolamine), the diluents microcrystalline cellulose and mannitol. According to WO2008136843, the use of diluents comprising reducing sugars should be avoided because these compounds may undergo a Maillard reaction with eltrombopag bis(monoethanolamine). Moreover, the use of diluents comprising coordinating metals should be avoided because of the fact that these metals may form an insoluble metal complex with eltrombopag bis(monoethanolamine).

The present invention provides a film-coated swallowable tablet comprising eltrombopag bis(monoethanolamine) and pharmaceutically acceptable excipients comprising calcium silicate as diluent. It was surprisingly found by the present inventors that, although calcium silicate contains the coordinating metal calcium, this diluent is applied in a tablet comprising eltrombopag bis(monoethanolamine) without causing any precipitating issues. In fact, the use of calcium silicate in the tablet comprising eltrombopag bis(monoethanolamine) provides a tablet with excellent disintegrating properties. The tablet exhibits very good stability and is bioequivalent to Revolade®/Promacta®. Moreover, the different tablet strengths are formulated in a dose proportional manner having the advantage that just one single blend is required to make all strengths.

The choice for calcium silicate as diluent for the tablet of the present invention is certainly not obvious. Calcium silicate is known in the art for its application as diluent in orally disintegrating tablet formulations because of its disintegrating properties, breaking the tablet down into easy to swallow fine particles. It is not self-evident for the person skilled in the art to use calcium silicate as diluent in film-coated swallowable tablet formulations.

In the tablet of the present invention, calcium silicate is present in an amount of 5 to 15% by weight based on the total weight of the tablet. By using this amount of calcium silicate, disintegration properties of the tablet are sufficiently improved, while still acceptable flow properties are obtained. More preferably, the amount of calcium silicate in the tablet is in the range of 7 to 13% by weight based on the total weight of the tablet.

The tablet of the present invention is preferably prepared by a process comprising wet granulation. The granulation process applied is simple and cost effective and includes a standard wet granulation technique.

The wet granulation process is performed with a granulation solvent selected from the group consisting of water, acetone, ethanol, isopropanol or a mixture thereof. The most preferred solvent to be used in accordance with the present invention is water.

At least 70% of the granules obtained by the process of wet granulation have a particle size between 90 and 355 μm. At least 45% of the granules have a particle size from 125 to 250 μm. Furthermore, maximum 15% of the granule particles are bigger than 355 μm and maximum 15% of the granules are smaller than 90 μm. By using granules with these particular particle size specifications, both good flow properties and compression performance are achieved. By limiting the amount of fines, sticking issues are prevented, while by limiting the amount of big granules, a good content uniformity is achieved.

The calcium silicate is preferably present in the extragranular phase of the tablet composition.

In a preferred embodiment, the tablet of the present invention comprises, besides calcium silicate, a diluent with good flow properties. Isomalt is a particularly preferred diluent to be used in combination with calcium silicate in the tablet of the present invention to improve the flow properties of the tablet composition. Moreover, isomalt is able to improve the compression performance of the tablet composition comprising calcium silicate. By using isomalt in the tablet of the present invention, the compression force needed to obtain the desired tablet hardness is significantly reduced. Generally, isomalt comprises a mixture of 6-O-α-D-glucopyranosyl-D-sorbitol (1,6-GPS) and 1-O-α-D-glucopyranosyl-D-mannitol dehydrate (1,1-GPM). 1,6-GPS is more soluble than 1,1-GPM. By shifting the ratio of the two components, the solubility and crystal water content can be adjusted. Preferably, the isomalt used in the tablet of the present invention is a grade comprising 1,6-GPS and 1,1-GPM in a ratio of 1:1. A typical and preferred example of a commercially available grade of isomalt, wherein 1,6-GPS and 1,1-GPM are present in a 1:1 ratio, is galenIQT™ 720. Preferably, the isomalt used in the present invention has a particle size distribution $D_{90}$ ranging from 300 to 400 μm. Most preferably, the particle size distribution $D_{90}$ ranges from 325 to 375 μm.

Additional advantage of isomalt is its intense and well-balanced sweet taste, which is very close to sucrose. It does not have any significant off-taste or aftertaste.

In the tablet of the present invention, isomalt is present in an amount of 25 to 50% by weight based on the total the weight of the tablet. More preferably, the amount of isomalt in the tablet is in the range of 30 to 42% by weight based on the total weight of the tablet.

The isomalt is preferably present in the extragranular phase of the tablet composition.

The film-coated swallowable tablet comprising eltrombopag bis(monoethanolamine) and calcium silicate as diluent further comprises pharmaceutically acceptable excipients. The excipients to be used in accordance with the present invention are well-known and are those excipients which are conventionally used by the person skilled in the art in pharmaceutical compositions. The excipients are selected from one or more diluents, binders, disintegrants, glidants or lubricants.

The diluent to be used in accordance with the present invention, in combination with calcium silicate, may be any diluent known to a person of ordinary skill in the art. Like mentioned before, a particularly preferred diluent to be used in combination with calcium silicate in the tablet of the present invention is isomalt. In addition to these diluents, one or more other diluents may be present in the film-coated swallowable tablet of the present invention. Preferably, these diluents are inorganic diluents, polysaccharides, mono- or disaccharides or sugar alcohols. Microcrystalline cellulose and mannitol are particularly preferred diluents.

The binder to be used in accordance with the present invention may be any binder known to a person of ordinary skill in the art. Suitable binders are selected from the group consisting of celluloses, starch, polyethylene glycol (PEG), sodium carboxymethylcellulose and polyvinyl pyrrolidone (PVP). PVP, also known as povidone, is a particularly preferred binder. The amount of binder in the film-coated swallowable tablet is between 1 and 5% by weight based on the total weight of the tablet. Preferably, the amount of binder in the tablet is between 1.5 and 4% by weight based on the total weight of the tablet. More preferably, the amount of binder in the tablet is between 2 and 3% by weight based on the total weight of the tablet.

The disintegrant to be used in accordance with the present invention may be any disintegrant known to a person of ordinary skill in the art. Suitable disintegrants to be used in accordance with the present invention are selected from the group consisting of croscarmellose sodium, crospovidone or sodium starch glycolate. Sodium starch glycolate is a particularly preferred disintegrant. The amount of disintegrant in the tablet is between 5 and 15% by weight based on the total weight of the tablet. Preferably, the amount of disintegrant in the tablet is between 8 and 12% by weight based on the total weight of the tablet.

The glidant to be used in accordance with the present invention may be any glidant known to a person of ordinary skill in the art. Colloidal silicon dioxide and talc are particularly preferred glidants.

The lubricant to be used in accordance with the present invention may be any lubricant known to a person of ordinary skill in the art. Magnesium stearate is a particularly preferred lubricant. The amount of lubricant in the film-coated swallowable tablet is between 0.5 and 2% by weight based on the total weight of the tablet.

The tablet of the present invention is coated by a film-coat. The coating serves cosmetic purposes. The coating material typically has no influence on the release rate, except of an inherent short initial delay in dissolution due to the time necessary to dissolve the coating.

The coating may be selected from amongst one or more of those suitable coating materials known in the art.

The coating may be performed by applying one or more film forming polymers, with or without other pharmaceutically inert excipients, as a solution/suspension. Coating is done using any conventional coating technique known in the art, such as spray coating in a conventional coating pan or fluidized bed processor; or dip coating.

The film-coated swallowable tablet of the present invention exhibits excellent long term stability. Moreover, the tablet of the present invention is very suitable for production on commercial scale making use of equipment and techniques commonly used in industry.

The film-coated swallowable tablets of the present invention are preferably packed in blister pack material. The blister pack material to be used in accordance with the present invention may be any blister pack material known to a person of ordinary skill in the art. Suitable blister pack materials to be used in accordance with the present invention are PVC/Alu, PVDC/PVC/Alu and Alu/Alu. A particularly preferred blister pack material to be used in accordance with the present invention is Alu/Alu.

The tablet composition according to the present invention displays dissolution behavior typical for immediate-release formulations.

The tablet composition in accordance with the present invention may be used as a medicament. The composition typically may be used in the treatment of immune thrombocytopenia (ITP), thrombocytopenia in patients with chronic hepatitis C virus (HCV) and severe aplastic anaemia (SAA).

The following examples are intended to illustrate the scope of the present invention but not to limit it thereto.

EXAMPLES

Example 1: Film-Coated Tablet Comprising Eltrombopag Bis(Monoethanolamine) and Calcium Silicate The film-coated tablet comprising eltrombopag bis(monoethanolamine) and calcium silicate has the composition as given in table 1.

TABLE 1

| Component | Tablet composition | |
|---|---|---|
| | mg/tablet | % |
| Intragranular components | | |
| Eltrombopag bis(monoethanolamine) | 95.70 | 19.94 |
| Microcrystalline cellulose | 30.72 | 6.40 |
| Mannitol | 63.36 | 13.20 |
| Povidone | 14.40 | 3.00 |
| Purified water | q.s. | q.s. |
| Extragranular components | | |
| Isomalt | 175.02 | 36.46 |
| Calcium silicate | 48.00 | 10.00 |
| Sodium starch glycolate | 48.00 | 10.00 |
| Magnesium stearate | 4.80 | 1.00 |
| Total core tablet weight | 480.00 | 100.00 |
| Opadry coating | 19.20 | 4.00 |
| Purified water | q.s. | q.s. |
| Total coated tablet weight | 499.20 | 104.00 |

The intragranular components were sieved to de-agglomerate and added to a high shear granulator bowl. Water was added until an adequate granule appearance was obtained. The obtained granulate was dried and sieved. The extragranular isomalt, calcium silicate and sodium starch glycolate were sieved to de-agglomerate and the excipients were mixed with the sieved granules in a diffusion mixer. The magnesium stearate was mixed, added to the diffusion mixer and the resulting mixture was mixed. The homogeneous blend was compressed on a rotary tablet press using appropriate punches.

The tablets obtained were packed in alu/alu blisters.

The invention claimed is:

1. A film-coated swallowable tablet comprising eltrombopag bis(monoethanolamine) and pharmaceutically acceptable excipients comprising calcium silicate as diluent and isomalt as diluent;
wherein the calcium silicate is present in an amount of 5 to 15% by weight based on the total weight of the tablet, and the isomalt is present in an amount of 25 to 50% by weight based on the total weight of the tablet.

2. The tablet according to claim 1, wherein the calcium silicate is present in an extragranular phase.

3. The tablet according to claim 1, wherein the isomalt has a particle size distribution $D_{90}$ ranging from 300 to 400 µm.

4. The tablet according to claim 2, wherein isomalt is present in the extragranular phase.

5. The tablet according to claim 1, wherein the pharmaceutically acceptable excipients are selected from one or more diluents, binders, disintegrants, glidants or lubricants.

6. The tablet according to claim 5, wherein the amount of binder is between 1 and 5% by weight based on the total weight of the tablet.

7. The tablet according to claim 6, wherein the binder is polyvinylpyrrolidone (PVP).

8. A process to prepare the tablet according to claim 1, comprising wet granulation.

9. The process according to claim 8, wherein at least 70% of the obtained granules have a particle size between 90 and 355 µm.

10. A method of treating immune thrombocytopenia (ITP), thrombocytopenia in patients with chronic hepatitis C virus (HCV) and/or severe aplastic anaemia (SAA) in a patient, which comprises administering the tablet according to claim 1 to a patient in need thereof.

11. The process according to claim 8, which comprises:
(i) wet granulating eltrombopag bis(monoethanolamine), a binder, and optionally additional pharmaceutically acceptable excipients to form a granulate;
(ii) combining said granulate with calcium silicate, isomalt, and optionally additional pharmaceutically acceptable excipients to form a tablet blend;
(iii) tableting said tablet blend to form a tablet; and
(iv) film coating said tablet.

12. The tablet according to claim 1, wherein said eltrombopag bis(monoethanolamine) is present in an intragranular phase and said calcium silicate is present in an extragranular phase.

13. The tablet according to claim 12, wherein said isomalt is present in said extragranular phase.

14. The tablet according to claim 13, wherein said intragranular phase further comprises a binder in an amount between 1 and 5% by weight based on the total weight of the tablet.

15. The tablet according to claim 14, wherein said binder is polyvinylpyrrolidone (PVP).

16. The tablet according to claim 15, wherein said intragranular phase further comprises a diluent.

17. The tablet according to claim 16, wherein said extragranular phase further comprises a disintegrant.

* * * * *